United States Patent

Hamada et al.

Patent Number: 4,629,795
Date of Patent: Dec. 16, 1986

[54] PROCESS FOR PREPARING IMIDAZOLE DERIVATIVES

[75] Inventors: Yoshinori Hamada, Hyogo; Shoji Shinomoto, Osaka; Isamu Yamada, Osaka; Haruo Koike, Osaka, all of Japan

[73] Assignee: Shionogi & Co., Ltd., Osaka, Japan

[21] Appl. No.: 729,869

[22] Filed: May 2, 1985

[30] Foreign Application Priority Data

May 25, 1984 [JP] Japan .................. 59-107237
May 25, 1984 [JP] Japan .................. 59-107238

[51] Int. Cl.$^4$ .................................. C07D 233/54
[52] U.S. Cl. ........................................... 548/341
[58] Field of Search .................................. 548/341

[56] References Cited

PUBLICATIONS

Noller, Textbook of Organic Chemistry, 3rd Ed., W. B. Saunders Co., Philadelphia, 1966, p. 139.

Primary Examiner—Henry R. Jiles
Assistant Examiner—Robert C. Whittenbaugh
Attorney, Agent, or Firm—Birch, Stewart, Kolasch & Birch

[57] ABSTRACT

An improved process for preparing a vinyl imidazole derivative (I) and a new method of production of a monoimidazole derivative (II) are provided:

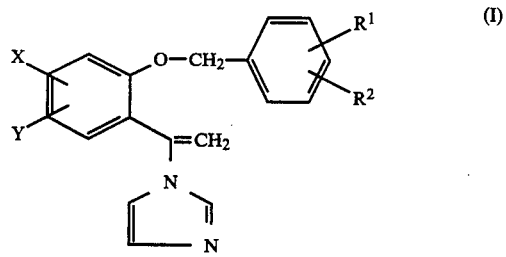

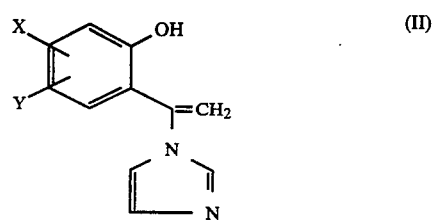

wherein $R^1$ is halogen; and $R^2$, X, and Y are each is hydrogen or halogen.

The vinyl imidazole derivatives (I) are useful as antimycotic agents for humans and animals or agricultural fungicides, and the monoimidazole derivatives (II) can be utilized as intermediates for preparing them.

6 Claims, 1 Drawing Figure

FIG. 1

PROCESS FOR PREPARING IMIDAZOLE DERIVATIVES

BACKGROUND OF THE INVENTION

1. Field of the Invention

The present invention relates to an improved process for preparing vinyl imidazole derivatives (I) which can be utilized as antimycotic agents for humans and animals or agricultural fungicides, and furthermore, it also relates to an improved method of production of useful monoimidazole derivatives (II). The monoimidazole derivatives are useful as intermediates for preparing the vinyl imizadole derivatives.

Specifically, the present invention relates to a method of preparation of compounds of the formula:

wherein $R^1$ is halogen, and $R^2$, X, and Y are each hydrogen or halogen.

2. Prior Art

(1) For example, the compounds (I) have been prepared by reacting 2-[1-(1H-imidazol-1-yl)vinyl]phenols with mono- or di-(halo-substituted)benzyl halogenide in the presence of a base such as sodium hydride in dried dimethylformamide (hereinafter referred to as "DMF") [U.S. Pat. No. 4,328,348].

(2) The monoimidazole derivatives (II), i.e., 2-[1-(1H-imidazol-1-yl)vinyl]phenols have been prepared by reacting o-hydroxyacetophenones (III) with 1,1'-thionyl diimidazole [U.S. Pat. No. 4,328,348], according to the following scheme:

wherein Hal is halogen, and $R^1$, $R^2$, X, and Y are each as defined above. In the prior art, the following problems still remain.

(i) Referring to the reaction for producing the compounds (I), (a) sodium hydride used as a base is expensive and extremely dangerous during the operation; (b) dried DMF as a solvent is easily decomposed in a base and difficult to effectively recover; (c) certain decomposed compounds from DMF may react with mono- or di-(halo-substituted)benzyl halogenide to give some by-products; and (d) the objective compound (I) is obtained in low yield because of the difficulty of separating the by-products therefrom.

(ii) In reference to the reaction for producing the monoimidazole derivatives (II), (a) a large amount of a 1H-imidazole (usually more than 2 mole equivalent) has to be used in the preparation of 1,1'-thionyl diimidazole which reacts with an o-hydroxyacetophenone (III); (b) the diimidazole compound (IV) of the formula:

wherein X and Y are each hydrogen or halogen is produced as a by-product in addition to the monoimidazole compound (II); and (c) therefore, the yield of the compound (II) is low and it has to be separated from the by-product (IV) by purification.

The present inventors have succeeded in solving the above problems (i) and (ii).

Referring to the problem (i), the present inventors have used safer and less expensive alkali metal hydroxide instead of sodium hydride; and they also found that dimethylamine resulting from the decomposition of DMF sometimes reacts with 4-chlorobenzyl bromide to give (4-chlorobenzyl)dimethylamine as a by-product and that a solvent containing dimethylsulfoxide can be used in place of DMF for avoiding the production of the (4-chlorobenzyl)dimethylamine to afford the vinyl imidazole derivatives (I) in high yield.

Regarding the problem (ii) the present inventors have found that half the amount of 1H-imidazole in the reaction medium is consumed in the production of 1,1'-thionyl diimidazole, that another half works as a base; and that the base can be replaced by other less expensive ones.

Furthermore, the present inventors have found that 1-halosulfinyl-1H-imidazole can be used in place of 1,1'-thionyl diimidazole prepared by reacting thionyl chloride with a 2 equimolar amount of 1H-imidazole.

Additionally, the present inventors have developed a process for converting a diimidazole (IV) into a monoimidazole (II) to increase the yield of the monoimidazole (II).

BRIEF SUMMARY OF THE INVENTION

The present invention relates to an improved process for preparing a vinyl imidazole derivative (I) and also an improved process for preparing a synthetic intermediate i.e., monoimidazole derivative (II).

The compounds (I) and (II) can be prepared according to the following reaction sequence:

wherein Hal, $R^1$, and Z are each halogen; $R^2$, X, and Y are each hydrogen or halogen.

The vinyl imidazole derivatives (I) are useful as antimycotic agents for humans and animals or agricultural fungicides, and the monoimidazole derivatives (II) can be utilized as intermediates for preparing them. [U.S. Pat. No. 4,328,348]

BRIEF DESCRIPTION OF THE DRAWINGS

No addition of an acid: ○-○
p-TsOH (0.1 mol equivalent): ●-●
p-TsOH (1.0 mol equivalent): ◐-◐
$BF_3.O(n-C_4H_9)_2$ (0.1 mol equivalent): □-□
$CF_3COOH$ (0.1 mol equivalent): ◆-■
MsOH (0.1 mol equivalent): △-△
$KHSO_4$ (0.1 mol equivalent): ▲-▲

DETAILED DESCRIPTION OF THE PREFERRED EMBODIMENTS OF THE INVENTION

Figure 1:
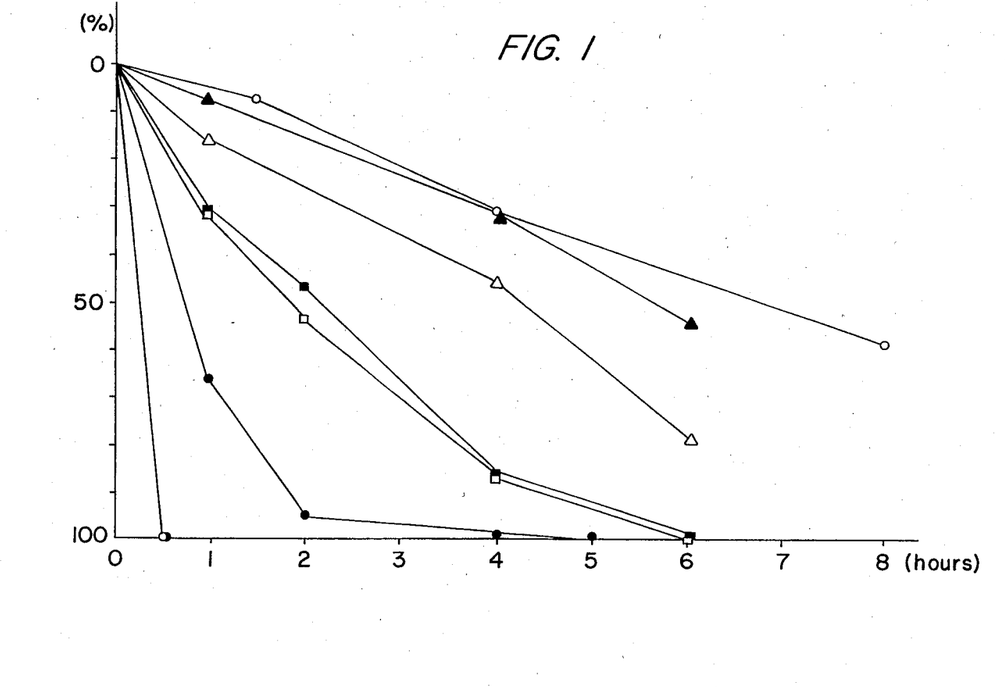
In FIG. 1, the conversion of the pure diimidazole derivative 5 to the corresponding monoimidazole derivative 4 as a function of time is shown by the curve, in which the vertical axis is the content (percentage, %) of the monoimidazole and the horizontal axis is reaction time (hour). Each mark on the curves indicates the following meanings.

The present invention relates to a process for preparing a compound of the formula (I):

wherein $R^1$ is halogen and $R^2$, X, and Y are each hydrogen or halogen
which comprises reacting a compound of the formula (II):

(II)

with mono- or di-(halo-substituted)benzyl halogenide in a solvent containing dimethylsulfoxide in the presence of an alkali metal hydroxide; and the present invention relates to a process for preparing a compound of the formula (I):

(I)

wherein $R^1$, $R^2$, X, and Y are each as defined above. which comprises reacting a compound of the formula (III):

(III)

with a 1-halosulfinyl-1H-imidazole in the presence of a base, and heating and/or treating the resulting mixture with an acid to give a compound of the formula (II):

(II)

and then reacting the latter with mono- or di-(halo-substituted)-benzyl halogenide in a solvent containing dimethylsulfoxide in the presence of an alkali metal hydroxide.

Furthermore, the present invention relates to a process for preparing a compound of the formula (II):

(II)

wherein X and Y are each hydrogen or halogen which comprises heating and/or treating a diimidazole derivative of the formula (IV) with an acid:

(IV)

and the present invention also relates to a process for preparing a compound of the formula (II):

(II)

wherein X and Y are each hydrogen or halogen which comprises reacting an ortho-hydroxyacetophenone of the formula (III):

(III)

with a 1-halosulfinyl-1H-imidazole in the presence of a base and then heating and/or treating the resulting mixture with an acid.

In the above definitions of $R^1$, $R^2$, X, Y, Hal, and Z, halogen includes fluorine, chlorine, bromine, and iodine.

The 1-halosulfinyl-1H-imidazole illustratively includes 1-chlorosulfinyl-1H-imidazole, 1-bromosulfinyl-1H-imidazole, and the like.

The vinyl imidazole derivatives (I) can easily be prepared from the o-hydroxyacetophenones (III) through the monoimidazole derivatives (II) according to the following reaction sequence.

Reaction Sequence

First Step:

(V)

wherein Hal, $R^1$, $R^2$, X, Y, and Z are each as defined above

FIRST STEP

In the first step, an o-hydroxyacetophenone (III) is allowed to react in the presence of a base in a pertinent solvent with a 1-halosulfinyl-1H-imidazole (VII) provided by reacting 1H-imidazole (V) with a thionyl halide (VI) in the presence of a base in an appropriate solvent to give a monoimidazole (II) and a diimidazole (IV).

Examples of the base used in this reaction are inorganic bases such as potassium carbonate, sodium carbonate, calcium carbonate, etc.: organic bases such as pyridine, picoline, trimethylamine, triethylamine, tri-n-propylamine, tri-n-butylamine, ethyldimethylamine, diethylmethylamine, n-propyldimethylamine, isopropyldimethylamine, tert-butyldimethylamine, n-butyldimethylamine, sec-butyldimethylamine, N-methylpyrrolidine, N-ethylpyrrolidine, N-methylpiperidine, N-ethylpiperidine, N-methylmorpholine, N-ethylmorpholine, quinuclidine, etc., preferably a base having an acid dissociation constant (pKa) higher than that of imidazole. As the solvent, halogenohydrocarbons (e.g., dichloromethane, dichloroethane, chloroform, etc.), aromatic solvents (e.g., benzene, toluene, etc.), ether solvents (e.g., ether, tetrahydrofuran, dioxane, etc.), dimethylsulfoxide, dimethylformamide, acetonitrile, and the like can be employed.

The reaction may be carried out at a temperature of about 100° C. to a temperature under cooling, preferably 50° to 0° C. and terminates within a period of from several minutes to several hours.

SECOND STEP

In the second step, a diimidazole (IV) is converted into a monoimidazole (II). The reaction may be conducted in an appropriate solvent with heating in the presence or absence of an acid or by an acid treatment at room temperature and accomplished for a period of from several minutes to several hours. As the acid, for example, inorganic acids (e.g., hydrochloric acid, sulfuric acid, phosphoric acid, potassium hydrogensulfate, etc.); sulfonic acids (e.g., p-toluenesulfonic acid, benzenesulfonic acid, methanesulfonic acid, trifluoromethanesulfonic acid, etc.); aliphatic acids of which the acidity is increased by one or more electron withdrawing groups such as fluorine, chlorine, and nitro (e.g., trifluoroacetic acid, trichloroacetic acid, etc.); organic acids (e.g., acetic anhydride, phthalic anhydride); and Lewis acids (e.g., boron trifluoride which may be used in an etherate form, aluminium chloride, zinc chloride, magnesium chloride, etc.) can be used. Representative of the solvents are aromatic solvents (e.g., benzene, toluene, xylene, etc.) and solvents (e.g., halogenohydrocarbons such as dichloromethane, dichloroethane, chloroform, etc.) which are not reactive with an acid. Heating is preferably carried out under reflux or at a temperature of higher than 80° C. The diimidazole (IV) can easily be converted into a monoimidazole (II) when a mixture of (II) and (IV) is allowed to react in the manner described above. Therefore the reaction may be continuously carried out from the first step to the second step.

THIRD STEP

In the third step, the monoimidazole (II) is allowed to react with mono- or di-(halo-substituted)benzyl halogenide in the presence of alkali metal hydroxide in dimethylsulfoxide (hereinafter referred to as "DMSO") or in a mixture of DMSO and other solvents to give a vinyl imidazole (I). DMSO may contain 5-10% water, and as the other solvents, halogenohydrocarbons such as dichloromethane, dichloroethane, etc.; ketone solvent such as acetone, methyl ethyl ketone, etc.; ether solvent such as tetrahydrofuran, glyme, diglyme, etc.; tetrahydrothiophen-1-oxide, sulfolane, dimethyl sulfone, dimethylimidazolidone, N-methylpyrrolidone, hexamethylphosphoramide, acetonitrile, and the like may be employed.

The alkali metal hydroxide may be exemplified by lithium hydroxide, sodium hydroxide, potassium hydroxide, and the like.

The mono- or di-(halosubstituted)benzyl halogenide means benzyl halogenide which is substituted by 1 or 2 halogens (e.g., fluorine, chlorine, bromine, iodine, etc.), and the benzyl halogenide means benzyl chloride, benzyl bromide, or benzyl iodide. The examples of the mono- or di-(halo-substituted)benzyl halogenide are 3-chlorobenzyl chloride, 3-chlorobenzyl bromide, 4-chlorobenzyl chloride, 4-chlorobenzyl bromide, 2,4-dichlorobenzyl chloride, 2,4-dichlorobenzyl bromide, 3,4-dichlorobenzyl chloride, 3,4-dichlorobenzyl bromide, and the like.

If required, a catalyst such as benzyl triethylammonium bromide, tetrabutylammonium iodide, tetrabutylammonium hydrogensulfate, and the like may be used.

The reaction can be conducted under cooling (about 0° C.) or at a temperature up to about 100° C., preferably about 10° C. to about 30° C. and terminates within a period of from several minutes to several hours.

The present invention will be explained in more detail by the following Examples.

EXAMPLE 1

2-[1-(1H-imidazol-1-yl)vinyl]phenol 4

(wherein Et is ethyl)

A solution of 325 g (4.77 mol) of 1H-imidazole 1 and 483 g (4.77 mol) of triethylamine in 3.3 L of dried dichloromethane was cooled to 0°–10° C. To the solution was dropwise added a solution of 568 g (4.77 mol) of thionyl chloride in 50 ml of dried dichloromethane in 50 minutes with stirring, and the mixture was stirred for a further 30 minutes to give imidazole reagent 2.

In another reaction pot, a solution of 500 g (3.67 mol) of o-hydroxyacetophenone 3 and 446 g (4.41 mol) of triethylamine in 0.6 L of dried dichloromethane was cooled to 0°–10° C. To the solution was added the suspension 2 above prepared before in 40 minutes and the mixture was stirred for 80 minutes at 0°–10° C. After the termination of the reaction the precipitating crystals were collected by filtration and the filtrate was evaporated under reduced pressure to give 1.67 kg of yellowish brown crystalline residue. To the crystalline residue was added 2 L of chilled water and then chilled solution of 73.4 g (1.84 mol) of sodium hydroxide dissolved in 2 L of water was added thereto with stirring. The mixture was stirred for another 1 hour and the precipitating crystals were collected by filtration, washed with 4 L of water and with 2 L of toluene, and dried in air to give 607 g (yield: 88.7%) of a mixture of 2-[1-(1H-imidazol-1-yl)vinyl]phenol 4 and 2-[1-(1,1-di-1H-imidazolyl)ethyl]phenol as pale pink crystals.

m.p. 145.5°–149° C.

The ratio of the monoimidazole 4 and the diimidazole 5 is 92% and 7.5% which was determined by high performance liquid chromatography (hereinafter referred to as "HPLC") analysis.

(ii)

The mixture of the monoimidazole 4 and the diimidazole 5 provided in the above step was suspended in 2.4 L of toluene. 2.3 g (0.012 mol) of p-Toluenesulfonic acid monohydrate (hereinafter referred to as "p-TsOH") was added to the suspension and the mixture was refluxed at the boiling point of toluene for 2 hours. The resulting mixture was allowed to stand for 25 minutes, cooled with water for 25 minutes, and then with ice for another 70 minutes. The precipitating pale brownish-white crystals were gathered by filtration, washed with 1.2 L of toluene, 0.3 L×3 of chilled acetone, and 0.9 L×2 of water successively; and then dried in air to give 561 g (yield: 82.0%) of pale grayish-white crystalline monoimidazole 4, m.p. 152°–153.5° C.

Anal. Calcd. (%) (for $C_{11}H_{10}N_2O$): C, 70.95; H, 5.41; N, 15.04; Found (%): C, 71.00; H, 5.17; N, 15.06.

IR: $\nu_{max}$(Nujol): 3140–2840, 2680, 2550, 1630, 1600 cm$^{-1}$.

NMR(d$_6$-DMSO): δ5.12 (s, 1H), 5.55 (s, 1H), 6.68–7.57 (m, 7H, aromatic H), 9.77 (broad, s, 1H, —OH).

The physical characteristics of the diimidazole 5:

m.p. 173.0°–173.5° C.

Anal. Calcd. (%) (for $C_{14}H_{14}N_4O$): C, 66.12; H, 5.55; N, 22.04 Found (%): C, 66.29; 1 H, 5.53; N, 22.06.

IR: $\nu_{max}$(Nujol): 3100–2600, 1599 cm$^{-1}$.

NMR(d$_6$-DMSO): δ2.68 (s, 3H CH$_3$—), 5.85 (d-d, J=2 Hz, 8 Hz, 1H), 6.63–7.57 (m, aromatic H), 9.98 (broad, s, 1H, —OH).

EXAMPLE 2-(a)–(g)

Pure diimidazole (Compound 5) was heated in the presence or absence of an acid in an appropriate solvent or treated with an acid at room temperature in an appropriate solvent. The mixture was evaporated, washed with water and/or a suitable solvent, and dried to give the monoimidazole (Compound 4).

(a) No addition of an acid

A mixture of 0.5 g (1.966 mmol) of pure compound 5 and 10 ml of toluene was heated at 130° C. for 8 hours. The resulting reaction mixture was evaporated, washed with water, and dried to give 0.4 g (yield: 100%) of crude crystals, m.p. 140°–145° C. The crude crystals contained the compound 5 and the compound 4 in the ratio of 40.6% and 59.4% which was determined by HPLC analysis.

(b) 0.1 mole equivalent of p-Toluenesulfonic acid monohydrate (hereinafter referred to as "p-TsOH") was used as an acid To a suspension of 1.0 g (3.93 mmol) of pure compound 5 in 20 ml of toluene was added 74.8 mg (0.1 mol equivalent) of p-TsOH and the mixture was heated under reflux for 130° C. for 5 hours. After the termination of the reaction the reaction mixture was cooled with ice under stirring for 1 hour and the precipitating cryltals were collected by filtration, washed with 4 ml of toluene and with 5 ml of water, and dried under reduced pressure to give 0.7 g (yield: 100%) of crude crystals, m.p. 152°–154° C. These crystals contained the compound 5 and the compound 4 in the ratio of 0.6% and 99.4% which was determined by HPLC analysis. Pure compound 4 was identical with an authentic specimen.

(c) 1.0 mol equivalent of p-TsOH was used as an acid:

A mixture of 0.5 g (1.966 mmol) of pure compound 5, 10 ml of toluene, and 0.374 g (1.0 mol equivalent) of p-TsOHH$_2$O was heated under reflux for 0.5 hours. The reaction mixture was evaporated, washed with water, and dried under reduced pressure to give 0.4 g (yield: 100%) of crude crystals, m.p. 152°–154° C. These crystals contained the compound 5 and the compound 4 in the ratio of 0.1% and 99.9% which was determined by HPLC analysis. Pure compound 4 was identical with an authentic specimen.

(d) 0.1 mol equivalent of boron trifluoride di-(n-butyl)ether (hereinafter referred to as "BF$_3$.O(n-C$_4$H$_9$)$_2$")

A mixture of 0.5 g (1.966 mmol) of pure compound 5, 10 ml of toluene, 38.9 mg (0.1 mol equivalent) of BF$_3$.O(n-C$_4$H$_9$)$_2$ was heated under reflux at 130° C. for 6 hours. The reaction mixture was evaporated to remove toluene, washed with water, and dried under reduced pressure to give 0.4 g (yield: 100%) of crude crystals, m.p. 150°–152° C. These crystals contained the compound 5 and the compound 4 in the ratio of 0.95% and 94.7% which was determined by HPLC analysis. Pure compound 4 was identical with an authentic specimen.

(e) 0.1 mol equivalent of trifluoroacetic acid (hereinafter referred to as "CF$_3$COOH") was used as an acid.

A mixture of 0.5 g (1.966 mmol) of pure compound 5, 10 ml of toluene, and 22 mg (0.1 mol equivalent) of CF$_3$COOH was heated under reflux at 130° C. for 6 hours. After removal of toluene, the reaction mixture was washed with water and dried under reduced pressure to give 0.4 g (yield: 100%) of crude crystals, m.p. 150°–152° C. These crystals contained the compound 5 and the compound 4 in the ratio of 1.1% and 98.9% which was determined by HPLC analysis. Pure compound 4 was identical with an authentic specimen.

(f) 0.1 mol equivalent of methanesulfonic acid (hereinafter referred to as "MsOH") was used as an acid.

A mixture of 0.5 g (1.966 mmol) of pure compound 5, 10 ml of toluene, 19 mg (0.1 mol equivalent) of MsOH was heated under reflux at 130° C. for 6 hours. The reaction mixture was evaporated, washed with water, and dried under reduced pressure to give 0.4 g (yield: 100%) of crude crystals, m.p. 145°–150° C. These crystals contained the compound 5 and the compound 4 in the ratio of 21.1% and 78.9% which was determined by HPLC analysis. Pure compound 4 was identical with an authentic specimen.

(g) 0.1 mol equivalent of potassium hydrogensulfate (hereinafter referred to as "KHSO$_4$").

A mixture of 0.5 g (1.966 mmol) of pure compound 5, 10 ml of toluene, and 27 mg (0.1 mol equivalent) of KHSO$_4$ was heated under reflux at 130° C. for 6 hours. After removal of toluene, the reaction mixture was washed with water and dried under reduced pressure to give 0.4 g (yield: 100%) of crude crystals m.p. 140°–145° C. These crystals contained the compound 5 and the compound 4 in the ratio of 45.1% and 54.9% which was determined by HPLC analysis. Pure compound 4 was identical with an authentic specimen.

The detailed reaction conditions and the content (percentage) of the monoimidazole in Example 2-(a)–(g) are shown in Table 1.

TABLE 1

| Acid amount | Diimidazole 5 amount, g(mmol) | Solvent amount, ml | Reaction temperature °C. | Reaction time hours | Content (percentage %) of Monoimidazole 4 after the reaction |
|---|---|---|---|---|---|
| No addition of an acid | 0.5(1.966) | toluene (10) | 130 | 8 | 59.4 |
| p-TsOH (74.8 mg, 0.1 eq. mol) | 1.0(3.93) | toluene (20) | 130 | 5 | 99.4 |
| p-TsOH (374 mg, 1.0 eq. mol) | 0.5(1.966) | toluene (10) | 130 | 0.5 | 99.9 |
| BF$_3$.O(n-C$_4$H$_9$)$_2$ (38.9 mg, 0.1 eq. mol) | 0.5(1.966) | toluene (10) | 130 | 6 | 94.7 |
| CF$_3$COOH (22 mg, 0.1 eq. mol) | 0.5(1.966) | toluene (10) | 130 | 6 | 98.9 |
| MsOH | 0.5(1.966) | toluene | 130 | 6 | 78.9 |

TABLE 1-continued

| Acid amount | Diimidazole 5 amount, g(mmol) | Solvent amount, ml | Reaction temperature °C. | Reaction time hours | Content (percentage %) of Monoimidazole 4 after the reaction |
|---|---|---|---|---|---|
| (19 mg, 0.1 eq. mol) KHSO$_4$ (27 mg, 0.1 eq. mol) | 0.5(1.966) | (10) toluene (10) | 130 | 6 | 54.9 |

Analysis for measuring a ratio of the monoimidazole 4 to the diimidazole 5 was achieved by HPLC of the following specifications.

Column: Nucleosil 5c-18,
Solvent: 0.02 mol aqueous diammonium hydrogen phosphate-acetonitrile,
Flow rate: 1.0 ml/min,
Detection: UV at 230 nm,
Chart speed: 0.5 cm/min.

EXAMPLE 3

2,5-dichloro-6-[1-(1H-imidazol-1-yl)vinyl]phenol 7

(wherein Et is ethyl)

To a solution of 99.6 mg (1.4625 mol, 1.5 mol equivalent) of 1H-imidazole and 0.204 ml (1.5 mol equivalent) of triethylamine in 1.5 ml of tetrahydrofuran (hereinafter referred to as "THF") was dropwise added 0.106 ml (1.5 mol equivalent) of thionyl chloride at 13°–17° C. The mixture was stirred at the same temperature for 30 minutes, and after the termination of the reaction the precipitating triethylamine hydrochloride was removed by filtration. The filtrate was dropwise added to a solution of 0.2 g (0.975 mmol) of 3,6-dichloro-2-hydroxy acetophenone 6, 0.163 ml (1.2 mol equivalent) of triethylamine and 0.5 ml of THF at 28°–32° C. The mixture was stirred at the same temperature for 1 hour and evaporated under reduced pressure. The residue was extracted with dichloromethane, and the extract was washed with water, dried over anhydrous sodium sulfate, and evaporated under reduced pressure. The resulting residue is purified by silica-gel chromatography to give 152 mg (yield: 61.0%) of the titled compound 7. m.p. 180°–182° C.

IR: $\nu_{max}$(Nujol) 1640, 1574 cm$^{-1}$.
NMR(CD$_3$OD): δ5.08, 5.83 (1H each, J=2 Hz, =<H/H), 6.99 (1H, d, J=9 Hz, aromatic H), 7.41 (1H, d, J=9 Hz, aromatic H).

In the above reaction the diimidazole compound 8 might be produced, but the compound 8 could be converted into the monoimidazole compound 7 in the same manner as described in Example 2.

EXAMPLE 4

1-{1-[2-(2,4-dichlorobenzyloxy)phenyl]vinyl}-1H-imidazole 10

To a solution of 500 g (2.69 mol) of 2-[1-(1H-imidazol-1-yl)vinyl]phenol 4 in 3 L of DMSO was added 210 g (3.22 mol) of potassium hydroxide (pellet) with stirring and the mixture was stirred at room temperature for 1 hour. The solution was cooled to 12°–18° C. and there was dropwise added a solution of 577 g (2.95 mol) of 2,4-dichlorobenzyl chloride 9 in 100 ml of DMSO in 1 hour. The mixture was allowed to stand at the same temperature with stirring for 2 hours. To the reaction mixture was dropwise added 4.5 L of water with ice-cooling in 45 minutes. The resulting mixture was stirred for 1 hour, and the precipitating crystals were collected by filtration, washed with water (0.75 L×4) and then with n-hexane (0.7 L×3), and dried in air to give 872 g (yield: 94.1%) of the titled compound 10, m.p., 90.5°–93° C.

Mass spectrum: m/e 344 (M+).
IR: $\nu_{max}$(Nujol): 3100, 1630, 1600 cm$^{-1}$.
UV: $\lambda_{max}$(EtOH): 281 nm (ε3200), 273 nm (ε2800).

NMR(CDCl₃): δ4.97 (s, 2H), 5.08 (d, J=1 Hz, 1H), 5.42 (d, J=1 Hz, 1H), 6.77-7.60 (m, 10H).

EXAMPLE 5

1-{1-[2-(3-Chlorobenzyloxy)phenyl]vinyl}-1H-imidazole hydrochloride 13

To a solution of 30 g (0.16 mol) of the compound 4 in 120 ml of DMSO was added 13.7 g (0.24 mol) of powdery potassium hydroxide with stirring. The mixture was cooled to 10°-15° C., and there was dropwise added 36.8 g of 3-chlorobenzyl chloride 11 in 1 hour.

The mixture was stirred at the same temperature for 2.5 hours. The reaction mixture was extracted with 600 ml of ice-water and with 300 ml of ethyl acetate, and the ethyl acetate layer was extraced with water (300 ml×3), dried over anhydrous sodium sulfate, and evaporated to give 71 g of glutinous residue 12.

Seventy-one grams of the above residue 12 was dissolved in 160 ml of ethyl acetate and a mixture of 2.45M gaseous hydrochloric acid in 67 ml of ethyl acetate was dropwise added thereto in 8 minutes. The mixture was stirred for 30 minutes, and the precipitating crystals were collected by filtration, washed with 100 ml of ethyl acetate, and dried to give 55.2 g (yield: 98.8%) of the titled compound 13 as pale yellowish white crystals, m.p., 148°-149° C. This was recrystallized from acetonitrile-ethyl acetate to give the titled compound 13 as white needles.

Anal Calcd. (%) (for $C_{18}H_{16}ON_2Cl_2$): C, 62.26; H, 4.65; N, 8.07; Cl, 20.4 Found (%): C, 62.24; H, 4.51; N, 8.09; Cl, 20.22.

Mass spectrum: m/e 310 (M+).

IR: $\nu_{max}$(Nujol): 2600-2400, 1657, 1559 cm⁻¹.

UV: $\lambda_{max}$(EtOH): 269 nm (ε2080), 277 nm (ε2690), 283.5 nm (ε2790).

NMR(CDCl₃): δ4.95 (s, 2H), 5.52 (1H, d, J=2 Hz), 6.02 (1H, d, J=2 Hz), 6.90-7.67 (10 H, m), 8.87 (1H, t, J=0.5 Hz).

What we claim is:

1. A process for preparing a compound of the formula:

wherein R¹ is halogen and R², X, and Y are each hydrogen or halogen, which comprises reacting a compound of the formula:

wherein X and Y each have the same meaning as defined above, with a 1-halosulfinyl-1H-imidazole in the presence of a base, and heating and/or treating with an acid the resulting mixture to give a compound of the formula:

wherein X and Y each have the same meaning as defined above and then reacting the latter with mono- or di-(halo-substituted)benzyl halogenide in a solvent containing dimethylsulfoxide in the presence of an alkali metal hydroxide.

2. A process for preparing a compound of the formula:

wherein X and Y are each hydrogen or halogen which comprises heating and/or treating with an acid a diimidazole derivative of the formula:

wherein X and Y each have the same meaning as defined above.

3. A process for preparing a compound of the formula:

wherein X and Y are each hydrogen or halogen which comprises reacting an ortho-hydroxyacetophenone of the formula:

wherein X and Y each has the same meaning as defined above with a 1-halosulfinyl-1H-imidazole in the presence of a base and then heating and/or treating with an acid the resulting mixture.

4. A process claimed in claim 1, wherein the acid is selected from the group consisting of hydrochloric acid, p-toluenesulfonic acid, methanesulfonic acid, trifluoroacetic acid, trifluoromethanesulfonic acid, boron trifluoride, and potassium hydrogensulfate.

5. A process claimed in claim 2, wherein the acid is selected from the group consisting of hydrochloric acid, p-toluenesulfonic acid, methanesulfonic acid, trifluoroacetic acid, trifluoromethanesulfonic acid, boron trifluoride, and potassium hydrogensulfate.

6. A process claimed in claim 3, wherein the acid is selected from the group consisting of hydrochloric acid, p-toluenesulfonic acid, methanesulfonic acid, trifluoroacetic acid, trifluoromethanesulfonic acid, boron trifluoride, and potassium hydrogensulfate.

* * * * *